United States Patent [19]

Yamada et al.

[11] Patent Number: 5,545,771
[45] Date of Patent: Aug. 13, 1996

[54] PROCESS FOR PREPARATION OF GEM-DIFLUOROALKANES

[75] Inventors: Toshiro Yamada, Kawasaki; Yasuo Imai, Tokyo; Yasuhiro Mitsuda, Kawasaki, all of Japan

[73] Assignee: Nippon Zeon Co., Ltd., Tokyo, Japan

[21] Appl. No.: 302,871

[22] PCT Filed: Mar. 12, 1993

[86] PCT No.: PCT/JP93/00301

§ 371 Date: Sep. 14, 1994

§ 102(e) Date: Sep. 14, 1994

[87] PCT Pub. No.: WO93/19027

PCT Pub. Date: Sep. 30, 1993

[30] Foreign Application Priority Data

Mar. 16, 1992 [JP] Japan .................. 4-090234

[51] Int. Cl.⁶ ........................................... C07C 17/08
[52] U.S. Cl. ............................................... 570/164
[58] Field of Search ............................................ 570/164

[56] References Cited

U.S. PATENT DOCUMENTS 2,287,934  10/1938  Grosse et al. .

FOREIGN PATENT DOCUMENTS

| 246651 | 2/1963 | Australia | 570/164 |
|---|---|---|---|
| 3903336 | 8/1990 | Germany . | |
| 39-26830 | 11/1964 | Japan . | |
| 52468 | 8/1965 | Japan . | |
| 63-27441 | 2/1988 | Japan . | |
| 217139 | 1/1990 | Japan . | |
| 5255143 | 10/1993 | Japan | 570/164 |
| 6100475 | 4/1994 | Japan | 570/164 |
| 3019027 | 9/1993 | WIPO | 570/164 |

OTHER PUBLICATIONS

Grosse, et al., J. Am. Chem. Soc., (1942), vol. 64, 2289–2291.

*Primary Examiner*—Alan Siegel
*Attorney, Agent, or Firm*—Sherman and Shalloway

[57] ABSTRACT

A process for preparation of a gem-difluoroalkane is provided which comprises (A) a step to add a fluorinated alkane having a boiling point of −30° to 30° to a crude alkyne having 3 or 4 carbon atoms containing a polymerizable olefin as an impurity, and distill the mixture to remove the polymerizable olefin, (B) a step to react hydrogen fluoride with the fluorinated alkane and the alkyne having 3 or 4 carbon atoms obtained in the above step to synthesize the gem-difluoroalkane, and (C) a step to distill the reaction solution of the above (B) to obtain the gem-difluoroalkane.

According to this process, gem-difluoroalkanes can be prepared more economically compared with usual processes.

16 Claims, No Drawings

PROCESS FOR PREPARATION OF GEM-DIFLUOROALKANES

This application is based on International application PCT/JP93/00301 filed Mar. 12, 1993.

Technical Field

The present invention relates to a process for preparation of gem-difluoroalkanes.

Background Technique

CFCs have hitherto been frequently used as cleaning agent, refrigerant, blowing agent or the like, but in accordance with a rise of concern about the problem of ozone layer depletion in recent years, it is internationally decided to restrict their use, and alternatives for CFCs are vigorously developed.

Fluorine compounds, as such or in the formation of polymers, can be expected as raw materials for highly functional materials in various fields including electronic industry and medical field.

In these circumstances, gem-difluoroalkanes represented by the general formula $RCF_2R'$ wherein R and R' denote hydrogen atoms or hydrocarbon residues optionally having substituent(s) are expected for uses as alternatives for CFCs, intermediates for syntheses of alternatives for CFCs, or raw materials for highly functional materials. For instance, 2,2-difluoropropane is used as a foaming agent, a refrigerant or the like (DE 3903336A and Japanese Laid-Open Patent Publication 17139/1990).

A process which comprises reacting an alkyne with hydrogen fluoride is known for preparation of a gem-difluoroalkane (U.S. Pat. No. 2,287,934 and J. Am. Chem. Soc., 64, 2289 (1942)).

However, there were problems in the above process. Alkynes, particularly low boiling alkynes such as propyne and butyne used as raw materials are extremely unstable substances, and hard to handle, and it takes much labor and costs in purification to obtain them in a pure form. In addition, the yields of the desired products are unsatisfactory and the process was disadvantageous in an economical aspect.

To solve these problems, a process is considered, which comprises using a crude alkyne containing a polymerizable olefin as an impurity, obtained as a distillate after naphtha cracking. Although this process is excellent in the points of economical efficiency and easiness in handling, there are problems that oligomers tend to be accessorily produced from the polymerizable olefins, and it is not easy to remove them by filtration or distillation.

Thus, since a crude alkyne is economically obtained as a distillate after naphtha cracking, a process is desired for preparing a gem-difluoroalkane simply and in good yields using the crude alkyne as a raw material, but the desire has not so far been attained.

Disclosure of Invention

The present invention has been made in view of the above circumstances, and aims at solving the problems in the usual processes and providing a process for preparing gem-difluoroalkanes more economically from crude alkynes.

According to the present invention, a process for preparation of a gem-difluoroalkane is provided which comprises (A) a step to add a fluorinated alkane having a boiling point of −30° to 30° C. to a crude alkyne having 3 or 4 carbon atoms containing a polymerizable olefin as an impurity, and distill the mixture to remove the polymerizable olefin, (B) a step to react hydrogen fluoride with the fluorinated alkane and the alkyne having 3 or 4 carbon atoms obtained in the above step to synthesize the gem-difluoroalkane, and (C) a step to distill the reaction solution of the above (B) to obtain the gem-difluoroalkane.

In the step (A) of the present invention, it is performed to add a fluorinated alkane having a boiling point of −30° to 30° C. to a crude alkane having 3 or 4 carbon atoms containing a polymerizable olefin as an impurity, and distill the mixture to remove the polymerizable olefin.

The crude alkyne can readily be obtained generally as a distillate after naphtha cracking, and contains an alkyne having 3 or 4 carbon atoms corresponding to the raw material of the desired gem-difluoroalkane. These alkynes include, for example, propyne, 1-butyne, 2-butyne.

The term "alkyne" in the present invention is intended to include an olefin such as allene or 1,2-butadiene which produces the same product as in propyne or 1-butyne by contact with hydrogen fluoride.

The impurity is a polymerizable olefin accompanying the alkyne, and includes, for example, a monoolefin such as ethylene, propylene, butene or pentene, and a diolefin such as 1,3-butadiene, isoprene or piperylene.

The purity of the crude alkyne is usually 10 wt % or more, and the ratio of the alkyne to the polymerizable olefin is usually 9/1 to 1/9 (mole ratio). There can, for example, be exemplified crude propyne containing propyne and polymerizable olefins containing propylene as a main component, obtained in the course of extracting propylene from the C3 distillate after naphtha cracking; crude propyne containing propyne and polymerizable olefins containing 1,3-butadiene as a main component, obtained in the course of extracting butadiene from the C4 distillate after naphtha cracking; crude 2-butyne containing 2-butyne and polymerizable olefins containing isoprene as a main component, obtained in the course of extracting isoprene from the C5 distillate after naphtha cracking; etc.

In the step (A), a fluorinated alkane is added to the crude alkyne. The fluorinated alkane is one having a boiling point of −30° to 30° C., and there can, for example, be exemplified 1,1-difluoroethane, 1,1,1,2-tetrafluoroethane, 2,2-difluoropropane, 2,2-difluorobutane, 1,1,1-trifluoro-2,2-dichloroethane, 1,1,1,2-tetrafluoro-2-chloroethane, 1,1-difluoro-1-chloroethane, etc. These fluorinated alkanes can be used alone or in combination of two or more.

Among these fluorinated alkanes, those not containing chlorine are preferably used in view of preservation of the environment.

It is preferable in the present invention to use a fluorinated alkane which has a boiling point as close as possible to that of an intended alkyne and does not azeotropically boil with the polymerizable olefin and the gem-difluoroalkane. For example, at least one compound selected from 1,1-difluoroethane, and 1,1,1,2-tetrafluoroethane is preferably used to propyne, and 2,2-difluorobutane to 2-butyne, respectively.

Distillation is performed at ordinary pressure or under pressurization, but preferably under pressurization in view of operability. Pressure is usually set to 10 kg/cm² (gage pressure) or less.

Distillation operation is performed in a batch system or continuously using a usual distillation tower.

By the above step (A) are obtained the fluorinated alkane and the crude alkyne having 3 or 4 carbon atoms from which the polymerizable olefin was removed. Since the crude alkyne is diluted with the fluorinated alkane, it is stable and extremely easy to handle.

Then, in the step (B), hydrogen fluoride is reacted with the fluorinated alkane and the alkyne having 3 or 4 carbon atoms obtained in the step (A) to synthesize a gem-difluoroalkane. The fluorinated alkane is inert to hydrogen fluoride, and not only produces no by-product, but brings about effects such as enhancement of the yield in the addition reaction between the alkyne and hydrogen fluoride.

The reaction can, usually, be performed by adding the mixture of the alkyne with the fluorinated alkane to hydrogen fluoride in a gaseous phase or a liquid phase. The use amount of hydrogen fluoride can suitably be selected in the range of usually 2 to 10 moles, preferably 2 to 5 moles per mole of the alkyne.

The reaction temperature is usually −70° to 100° C., preferably −30° to 30° C. The reaction time varies depending on the kind and use amount of raw materials, reaction temperature, etc., but is usually 0.5 to 10 hours, preferably 0.5 to 5 hours.

The reaction method varies depending on the kind of raw materials, reaction temperature, etc., but the reaction is usually performed under a pressure of 10 kg/cm$^2$ or less in a closed reactor.

As a specific example of the reaction method is mentioned a method which comprises putting hydrogen fluoride in a closed reactor such as an autoclave; when it reaches a predetermined temperature, the alkyne and the fluorinated alkane are added while the system is maintained at that temperature; the mixture is held at the predetermined temperature for a certain time and then held at a temperature equal to or higher than room temperature to complete the reaction.

After the reaction is completed, the reaction solution is distilled in the step (C) to isolate the gem-difluoroalkane. By the distillation operation, the desired product can be separated from excessive hydrogen fluoride, reaction by-products and the fluorinated alkane.

The distillation can be performed according to a usual method, as in the above step (A).

INDUSTRIAL APPLICABILITY

Thus, it is possible, according to the present invention, to obtain a gem-difluoroalkane from a crude alkyne containing a polymerizable olefin, by a simple and economical process, in a high yield even compared with the usual process using a highly pure raw material.

BEST MODE OF CARRYING OUT THE INVENTION

The present invention is further specifically described below according to examples. Parts and % in the examples and the comparative examples are based on weight, unless otherwise defined.

EXAMPLE 1

100 g of 1,1-difluoroethane was added to 200 g of a mixture of 50 wt % of butadiene and 50 wt % of propyne, and distillation was performed in a distillation tower having a theoretical plate number of 20 to give 180 g of a mixture of 50 wt % of propyne and 50 wt % of 1,1-difluoroethane. The boiling point was 20° C./5 atm and the distillation yield was 90%.

Then, 150 g of anhydrous hydrogen fluoride was put in an autoclave and cooled to −20° C. under stirring, 180 g of a mixture 50 wt % of propyne with 50 wt % of 1,1-difluoroethane was gradually introduced in a gaseous state thereinto to let the inner temperature rise to room temperature, and the reaction mixture was stirred for one hour.

After completion of the reaction, the reaction solution was distilled to remove the anhydrous hydrogen fluoride and the accessorily produced polymer, and the distillate was further rectified to distill off 1,1-difluoroethane, and thereby 147 g of 2,2-difluoropropane was obtained from the bottom part of the distillation tower (boiling point : 25° C./5.8 atm, purity: 99%).

EXAMPLE 2

The same operations as in Example 1 were performed except that the 1,1-difluoroethane was replaced by 1,1,1,2-tetrafluoroethane to give 141 g of 2,2-difluoropropane.

EXAMPLE 3

The same operations as in Example 1 were performed except that the butadiene and the 1,1-difluoroethane were replaced by propylene and 1,1,1,2-tetrafluoroethane, respectively to give 140 g of 2,2-difluoropropane.

We claim:

1. A process for preparation of a gem-difluoroalkane which comprises
   (A) adding a fluorinated alkane having a boiling point of −30° to 30° C. to a crude mixture containing allene, 1,2-butadiene or alkyne having 3 or 4 carbon atoms and a polymerizable olefin as an impurity, and distilling the mixture to remove the polymerizable olefin,
   (B) reacting hydrogen fluoride with the fluorinated alkane and the allene, 1,2-butadiene or alkyne having 3 or 4 carbon atoms obtained in the above step to synthesize the gem-difluoroalkane, and
   (C) distilling the reaction solution of the above (B) to obtain the gem-difluoroalkane.

2. The process for preparation of the gem-difluoroalkane according to claim 1 wherein the crude mixture in the step (A) is a crude mixture containing the alkyne having 3 or 4 carbon atoms and the polymerizable olefin as an impurity, obtained as a distillate after naphtha cracking.

3. The process for preparation of the gem-difluoroalkane according to claim 2 wherein the alkyne having 3 or 4 carbon atoms is propyne, 1-butyne or 2-butyne.

4. The process for preparation of the gem-difluoroalkane according to claim 1 wherein the polymerizable olefin in the crude mixture in step (A) is a monolefin or a diolefin.

5. The process for preparation of the gem-difluoroalkane according to claim 4 wherein the crude mixture contains the monolefin which is ethylene, propylene or pentane.

6. The process for preparation of the gem-difluoroalkane according to claim 4 wherein the crude mixture contains the diolefin which is 1,3-butadiene, isoprene or piperylene.

7. The process for preparation of the gem-difluoroalkane according to claim 1 wherein the purity in the crude mixture of allene, 1,2-butadiene or alkyne in the step (A) is 10 wt % or more.

8. The process for preparation of the gem-difluoroalkane according to claim 1 wherein the molar ratio of allene, 1,2-butadiene or the alkyne to the polymerizable olefin in the crude mixture in step (A) is 9/1 to 1/9.

9. The process for preparation of the gem-difluoroalkane according to claim 1 wherein the fluorinated alkane is 1,1-difluoroethane, 1,1,1,2-tetrafluoroethane, 2,2-difluoropropane, 2,2-difluorobutane, 1,1,1-trifluoro-2,2-dichloroethane, 1,1,1,2-tetrafluoro-2-chloroethane or 1,1-difluoro-1-chloroethane.

10. The process for preparation of the gem-difluoroalkane according to claim 1 wherein the crude mixture in step (A) is a distillate after naphtha cracking comprising allene and the polymerizable olefin.

11. The process for preparation of the gem-difluoroalkane according to claim 1 wherein the crude mixture in step (A) is a distillate after naphtha cracking comprising 1,2-butadiene and the polymerizable olefin.

12. The process for preparation of the gem-difluoroalkane according to claim 1, wherein the fluorinated alkane is 1,1-difluoroethane, 1,1,1,2-tetrafluoroethane, 2,2-difluoropropane, or 2,2-difluorobutane.

13. The process for preparation of the gem-difluoroalkane according to claim 1 wherein the crude mixture contains propyne as the alkyne having 3 or 4 carbon atoms and wherein the fluorinated alkane is 1,1-difluoroethane, 1,1,1,2-tetrafluoroalkane, or mixture thereof.

14. The process for the preparation of the gem-difluoroalkane according to claim 1 wherein the crude mixture contains 2-butyne as the alkyne have 3 or 4 carbon atoms and wherein the fluorinated alkane is 2,2-difluorobutane.

15. The process for the preparation of the gem-difluoroalkane according to claim 1 wherein step (B) comprises adding the fluorinated alkane and 1,2-butadiene or alkyne from step (A) to hydrogen fluoride in a gaseous phase or liquid phase at a molar ratio of hydrogen fluoride to allene, 1,2-butadiene or alkyne of from 2/1 to 5/1, at a temperature of from −30° to 30° C.

16. The process according to claim 1 wherein the gem-difluoroalkane is 2,2-difluoropropane.

\* \* \* \* \*